(12) United States Patent
Swetlik et al.

(10) Patent No.: US 7,091,879 B2
(45) Date of Patent: Aug. 15, 2006

(54) SYSTEM AND METHOD FOR USING MULTIPLE MEDICAL MONITORS

(75) Inventors: Donald Edward Swetlik, Temecula, CA (US); Robert Edward Whitten, Tujunga, CA (US); Richard Brian Paul, Diamond Bar, CA (US); Gary Bruce Edstrom, Glendale, CA (US); Gary Michael Zednik, Agua Dulce, CA (US); Celso Ochoa Decastro, Jr., Northridge, CA (US); Roy Seizo Carr, Chatsworth, CA (US)

(73) Assignee: Invivo Corporation, Orlando, FL (US)

( * ) Notice: Subject to any disclaimer, the term of this patent is extended or adjusted under 35 U.S.C. 154(b) by 627 days.

(21) Appl. No.: 10/066,549

(22) Filed: Feb. 5, 2002

(65) Prior Publication Data

US 2003/0146847 A1    Aug. 7, 2003

(51) Int. Cl.
    G08B 21/00    (2006.01)
(52) U.S. Cl. ............... 340/870.16; 128/903; 600/300
(58) Field of Classification Search ........... 340/870.16; 128/903; 600/300, 382
    See application file for complete search history.

(56) References Cited

U.S. PATENT DOCUMENTS

| | | | |
|---|---|---|---|
| 3,832,994 A | 9/1974 | Bicher et al. ............ 128/2.06 A |
| 3,898,984 A | 8/1975 | Mandel et al. ............ 128/2.1 A |
| 3,921,621 A * | 11/1975 | Baessler ...................... 600/549 |
| 3,943,918 A | 3/1976 | Lewis ........................ 128/2.1 A |
| 3,986,498 A | 10/1976 | Lewis ....................... 128/2.06 R |
| 4,531,526 A | 7/1985 | Genest ........................ 128/630 |
| 4,536,486 A | 8/1985 | Lewis .......................... 502/74 |
| 4,562,840 A | 1/1986 | Batina et al. ............. 128/419 PT |
| 4,658,831 A | 4/1987 | Reinhard et al. ............. 128/697 |
| 4,827,943 A | 5/1989 | Bornn et al. ................. 128/668 |
| 4,857,716 A | 8/1989 | Gombrich et al. ............ 235/462 |
| 5,002,064 A | 3/1991 | Allain et al. ................ 128/710 |
| 5,027,825 A * | 7/1991 | Phelps et al. ............... 600/528 |
| 5,029,590 A | 7/1991 | Allain et al. ................ 128/710 |
| 5,036,869 A | 8/1991 | Inahara ....................... 128/903 |
| 5,131,399 A | 7/1992 | Sciarra ....................... 128/671 |
| 5,153,584 A | 10/1992 | Engira .................... 340/870.18 |
| 5,157,604 A | 10/1992 | Axford et al. ........... 364/413.03 |
| 5,205,294 A | 4/1993 | Flach et al. ................. 128/696 |
| 5,307,818 A | 5/1994 | Segalowitz ................. 128/696 |
| 5,322,069 A | 6/1994 | Gallant et al. .............. 128/700 |
| 5,333,617 A | 8/1994 | Hafner ........................ 128/697 |
| 5,335,664 A | 8/1994 | Nagashima ................. 128/696 |
| 5,458,122 A | 10/1995 | Hethuin ...................... 128/696 |
| 5,458,124 A | 10/1995 | Stanko et al. ............... 128/696 |
| 5,462,051 A | 10/1995 | Oka et al. ................... 128/630 |

(Continued)

Primary Examiner—Timothy Edwards, Jr.
(74) Attorney, Agent, or Firm—Boyle Fredrickson Newholm Stein & Gratz S.C.

(57) ABSTRACT

The present invention relates to a system and method for simultaneously using and configuring one or more disposable transmitters. The system includes at least one single or multiple use disposable transmitter, a central station, and a receiver module. The transmitter is connected to a patient to gather and measure biomedical information. The transmitter transmits the biomedical information through the receiver module to the central station for processing, storage and display. Prior to use, each transmitter must be configured to work with the central station and the receiver module. This allows the users to configure the disposable transmitters relatively quickly and easily without needing advanced technical information. The inventive configuration also enables the operator to map a location on a monitor in the central station to a specific disposable transmitter and ultimately to a specific patient or location in the coverage area that is covered by the system.

18 Claims, 8 Drawing Sheets

U.S. PATENT DOCUMENTS

| | | | | |
|---|---|---|---|---|
| 5,464,021 A | 11/1995 | Birnbaum | ............... | 128/696 |
| 5,511,553 A | 4/1996 | Segalowitz | ............... | 128/696 |
| 5,534,851 A | 7/1996 | Russek | ............... | 340/573 |
| 5,568,814 A | 10/1996 | Gallant et al. | ............... | 128/672 |
| 5,687,734 A | 11/1997 | Dempsey et al. | ............... | 128/696 |
| 5,690,119 A | 11/1997 | Rytky et al. | ............... | 128/706 |
| 5,718,234 A * | 2/1998 | Warden et al. | ............... | 600/300 |
| 5,844,862 A | 12/1998 | Cocatre-Zilgien | ............... | 368/10 |
| 5,855,609 A | 1/1999 | Knapp | ............... | 623/11 |
| 5,862,803 A | 1/1999 | Besson et al. | ............... | 128/696 |
| 5,877,675 A | 3/1999 | Rebstock et al. | ............... | 340/286.07 |
| 5,907,291 A | 5/1999 | Chen et al. | ............... | 340/870.16 |
| 5,935,099 A | 8/1999 | Peterson et al. | ............... | 604/65 |
| 5,936,539 A | 8/1999 | Fuchs | ............... | 340/825.07 |
| 5,944,659 A | 8/1999 | Flach et al. | ............... | 600/300 |
| 5,950,632 A | 9/1999 | Reber et al. | ............... | 128/898 |
| 5,957,838 A | 9/1999 | Rantala | ............... | 600/300 |
| 5,957,854 A | 9/1999 | Besson et al. | ............... | 600/509 |
| 5,966,692 A | 10/1999 | Langer et al. | ............... | 705/3 |
| 6,050,940 A * | 4/2000 | Braun et al. | ............... | 600/300 |
| 6,066,093 A | 5/2000 | Kelly et al. | ............... | 600/386 |
| 6,083,248 A | 7/2000 | Thompson | ............... | 607/30 |
| 6,093,146 A | 7/2000 | Filangeri | ............... | 600/300 |
| 6,102,857 A | 8/2000 | Kruger | ............... | 600/437 |
| 6,104,295 A * | 8/2000 | Gaisser et al. | ............... | 340/573.4 |
| 6,150,951 A | 11/2000 | Olejniczak | ............... | 340/825.03 |
| 6,160,047 A | 12/2000 | Agostini et al. | ............... | 524/494 |
| 6,160,478 A | 12/2000 | Jacobsen et al. | ............... | 340/539 |
| 6,161,036 A | 12/2000 | Matsumura et al. | ............... | 600/509 |
| 6,167,412 A | 12/2000 | Simons | ............... | 708/105 |
| 6,213,942 B1 | 4/2001 | Flach et al. | ............... | 600/300 |
| 6,225,549 B1 | 5/2001 | Holland | ............... | 136/205 |
| 6,229,454 B1 | 5/2001 | Heikkilä et al. | ............... | 340/870.14 |
| 6,238,338 B1 | 5/2001 | DeLuca et al. | ............... | 600/300 |
| 6,240,317 B1 | 5/2001 | Villaseca et al. | ............... | 607/60 |
| 6,248,067 B1 | 6/2001 | Causey, III et al. | ............... | 600/365 |
| 6,285,899 B1 | 9/2001 | Ghaem et al. | ............... | 600/391 |
| 6,287,252 B1 * | 9/2001 | Lugo | ............... | 600/300 |
| 6,292,687 B1 | 9/2001 | Lowell et al. | ............... | 600/515 |
| 6,416,471 B1 * | 7/2002 | Kumar et al. | ............... | 600/300 |
| 6,454,709 B1 * | 9/2002 | Kleinschmidt et al. | ............... | 600/300 |
| 6,494,829 B1 * | 12/2002 | New et al. | ............... | 600/300 |
| 2002/0084903 A1 * | 7/2002 | Chaco | ............... | 340/573.1 |
| 2003/0032446 A1 * | 2/2003 | Pincus | ............... | 455/556 |

* cited by examiner

Fig. 1    100

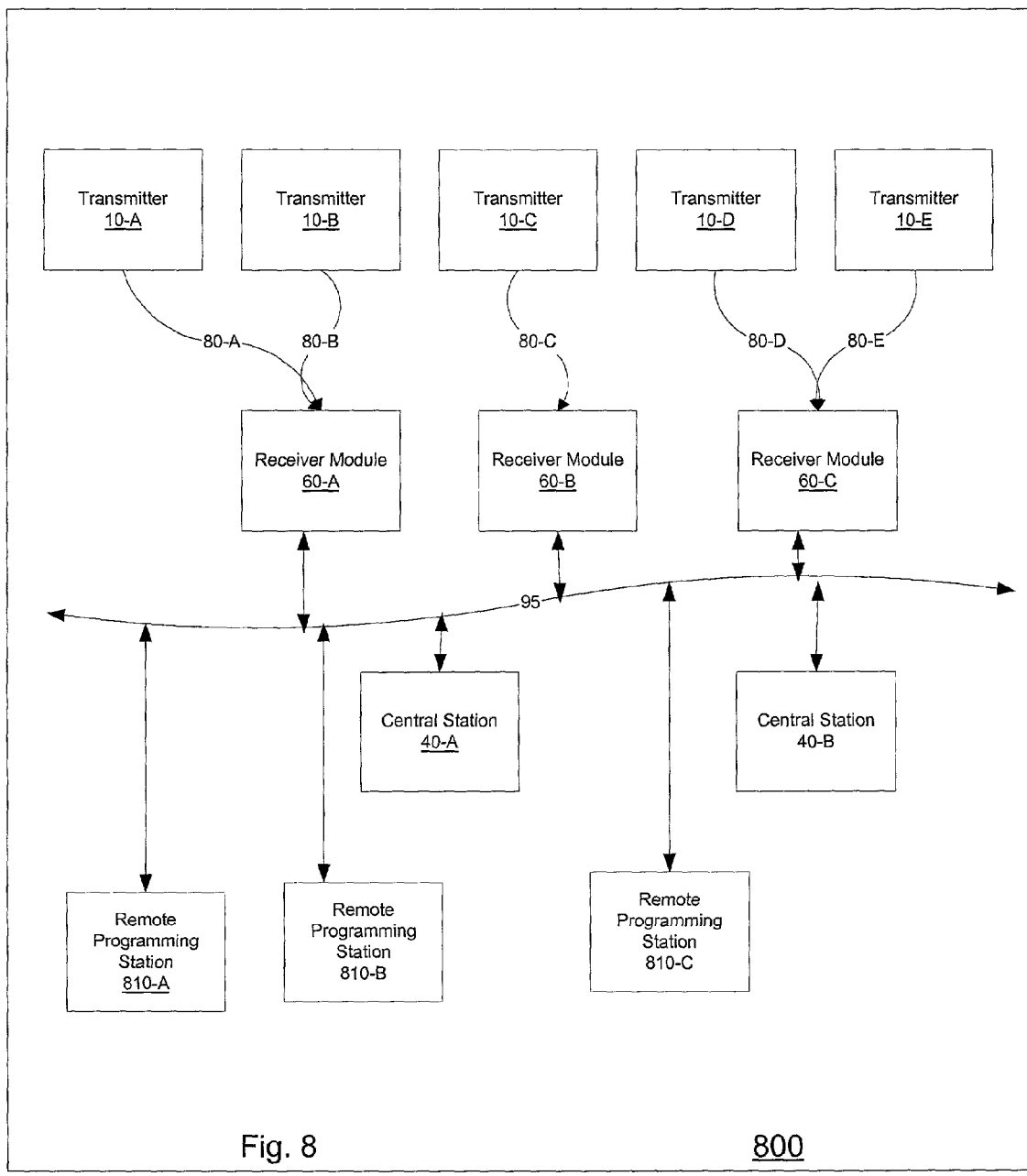
Fig. 8                                800

SYSTEM AND METHOD FOR USING MULTIPLE MEDICAL MONITORS

FIELD OF THE INVENTION

This invention relates to medical monitoring systems, and more particularly to telemetry systems with disposable and/or reusable transmitters.

BACKGROUND OF THE INVENTION

In order to effectively monitor very ill patients, they often are connected to monitoring systems, such as telemetry systems. These systems generally include a number of monitors, such as ECG devices and reusable transmitters, for obtaining and measuring biomedical information from connected patients. Note that while different types of monitors are used in telemetry systems, typical systems using transmitters use reusable transmitters. Most reusable transmitters require replaceable and standardized batteries and electrodes to properly obtain and measure information from connected patients. Upon obtaining information from a connected patient, each reusable transmitter transmits the information to a central station, which receives information from multiple monitors and processes, displays and stores the received information. In current telemetry systems, there is a considerable safety issue in associating information in the central station with the appropriate transmitter and ultimately the appropriate patient.

Reusable transmitters are relatively expensive items that must be tracked and managed over long periods of time. Currently, not all batteries or electrodes work with all reusable transmitters. Therefore, batteries and electrodes used in these transmitters also must be managed, tracked and replenished. Moreover, transmitters are usually subjected to very extreme conditions and failure is not uncommon. Hence, considerable time is spent troubleshooting problems in telemetry systems. Additionally, clinical environments are busy and fast paced. Therefore, relatively expensive reusable transmitters are easily lost, removed from the premises, and/or discarded.

In order to obtain required information from patients, transmitters are usually worn for extended periods of time. This often causes the transmitters to become soiled by various bodily fluids. Thus, the transmitters must be cleaned between patients' uses and at other times when they are soiled. However, due to the complex mechanical construction of reusable transmitters, cleaning is generally labor intensive and unpleasant and may not be thoroughly performed.

Reusable transmitters are generally bulky which make them uncomfortable for patients to wear for extended periods of time, especially while sleeping. However, due to the expense associated with most reusable transmitters, there is a minimum size requirement to prevent loss. For example, most manufacturers require that the sizes of their reusable transmitters be such that they can not be flushed down a toilet.

To solve the above mentioned problems, a current telemetry system uses a single disposable transmitter, as set forth in U.S. Pat. No. 5,718,234. However, the disposable transmitter, described therein, can only transmit information to a device, such as a central station, which accepts one transmission at a time. Thus, there can be no other active transmitters in the area where the disposable transmitter is being used. Most telemetry applications require using multiple transmitters on many different patients at the same time. Thus, to be logistically practical, preferably multiple disposable telemetry transmitters are used simultaneously and/or with reusable transmitters and information transmitted from each disposable transmitter must be properly associated with the transmitter and the connected patient.

Therefore, in telemetry systems where there are multiple transmitters, an efficient system must be created for configuring different types of transmitters and for associating the correct data with each transmitter.

SUMMARY OF THE INVENTION

The present invention relates to a system and method for simultaneously using and configuring one or more disposable and/or non-disposable transmitters. In one embodiment, the system includes at least one single use disposable transmitter, a central station, and a receiver module. The transmitter is connected to a patient to gather and measure biomedical information. The transmitter transmits the biomedical information through the receiver module to the central station for processing, storing and displaying. Prior to use, each transmitter must be configured to work with the central station and the receiver module. This allows the users to configure the disposable transmitters relatively quickly and easily without needing advanced technical experience or information. The system configuration also enables the operator to map a location on a monitor in the central station to a specific disposable transmitter and ultimately to a specific patient or location in the coverage area that is covered by the system.

Specifically, in a preferred embodiment of the invention, the system includes several channels, preferably wireless channels, for transmitting data between the transmitter and the receiver module. Each wireless channel is configured for use by one transmitter and receiver module and mapped to the central station. Each disposable transmitter includes one or more processing units for processing biomedical data gathered from a patient. In a preferred embodiment, after processing the biomedical data, the transmitter sends the data to the receiver module via a wireless channel. The receiver module includes components that format the data for further transmission to the central station.

The central station includes a display and a processing base for processing and storing incoming data. The processing base operates the display, and includes a transmitter programming interface for programming and configuring transmitters and an output component for displaying information and for generating print outs of biomedical data. The display screen is divided into multiple patient tiles and/or regions for displaying information, controls, and instructions. Each patient tile is on a predetermined portion of the screen, e.g. a rectangular portion; and each tile includes several regions for displaying patient information.

According to the invention in a wireless environment, during configuration of a disposable transmitter, each tile associated with the disposable transmitter is associated with a specific radio frequency. The radio frequency represents the channel into which the receiver associated with the tile is tuned. Once a tile is associated with a transmitter, the location of the tile is generally static on the display. This enables the operator of the system to associate a tile with a transmitter and ultimately a patient and/or location in the coverage area.

The software for operating the central station includes multiple Virtual Patient Objects (VPO). Each patient's tile is mapped to one VPO and each VPO also is mapped to one receiver object. Each receiver object maintains control of one receiver and the receiver object retains information necessary to configure the receiver to a fixed wireless channel. During operation, biomedical information flows from the transmitter through the receiver and the receiver object into memory in the central monitor station. Thereafter, the information is transmitted to the VPO for display in an associated patient tile. The VPO associated with each tile maintains knowledge of whether or not a patient is admitted to the tile.

Prior to using the system, the operator must configure each disposable transmitter to work with the central station. During configuration, the operator connects a programming port of a new transmitter into the transmitter programming interface of the central station. The programmer object software in the central station detects the presence of the new transmitter and notifies a command processor. The command processor instructs the operator to select a patient tile that is to be associated with the new transmitter. If a patient is already associated with the tile, the system instructs the operator to use a new tile, deactivate the transmitter associated with the tile and/or discharge the patient that is currently associated with the tile. If there is no patient associated with the tile, the system determines if an active transmitter is assigned to the wireless channel that is used by the tile. If an active transmitter is detected, the system instructs the operator to deactivate the active transmitter. Thereafter, the system programs the transmitter with the frequency associated with the tile and the transmitter's serial number is stored in the tile. The transmitter's serial number is also included in transmitted data packets from the transmitter. The associated tile uses the serial number to identify and only display data from the appropriate transmitter. In one embodiment, the user is then instructed to enter identifying patient data into the display screen and to write the patient's name on the associated transmitter.

According to the invention, each transmitter is marked with disposal instructions in order to deactivate and dispose of the transmitter after use. Alternatively, each transmitter may deactivate and disable itself after being disconnected from the patient for a predetermined amount of time.

In another embodiment of the invention, the system may include one or more remote programming stations that may be included in several locations in a coverage area or in remote locations. The remote programming station may duplicate the central station's display, showing the same data and allowing the same interactions as the central station's display or it may be programmed in other ways to display and receive other information.

Additional features and advantages of the invention will be set forth in the description that follows, and in part will be apparent from the description, or may be learned by practice of the invention. Certain objectives and advantages of the invention will be realized and attained by the system particularly pointed out in the written description and claims hereof as well as the appended drawings.

To achieve these and other advantages and in accordance with the purpose of the invention, as embodied and broadly described, the present invention provides a computer driven system for processing biomedical data from at least one patient, including: one or more disposable transmitters that are each connected to one patient to obtain biomedical data from the patient. Each disposable transmitter includes a connection for obtaining biomedical data from a patient, one or more processing components for processing biomedical data from the patient, and one or more transmitters for transmitting the biomedical data; one or more receiving components for receiving biomedical data from the disposable transmitters; and a central station for processing, storing and displaying the biomedical data. The central station includes a configuration component for configuring each disposable transmitter prior to use and for associating biomedical data from each disposable transmitter with a specific region on a display in the central station.

BRIEF DESCRIPTION OF THE DRAWINGS

The accompanying drawings, which are included to provide a further understanding of the invention and are incorporated in and constitute a part of this specification, illustrate embodiments of the invention that together with the description serve to explain the principles of the invention.

In the drawings:

FIG. 8 illustrates a medical telemetry system with a plurality of remote central stations.

DETAILED DESCRIPTION

Reference will now be made in detail to the preferred embodiments of the present invention, examples of which are illustrated in the accompanying drawings. In one embodiment, the present invention extends the functionality of the inventive system and method for configuring and using multiple disposable transmitters in a telemetry system.

Figure 1:
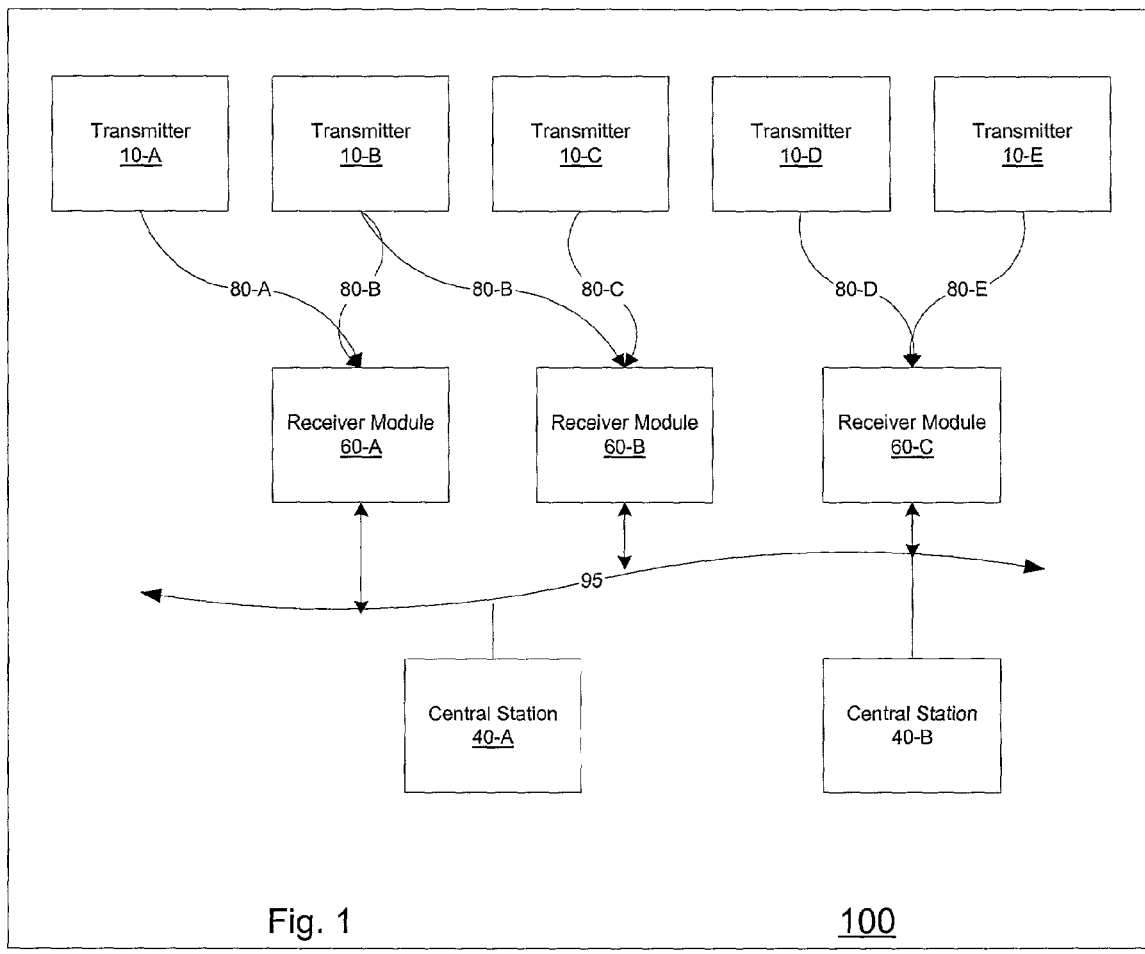
FIG. 1 illustrates a medical system used in the invention.

FIG. 1 illustrates a medical system 100 that comprises multiple transmitters (10A–10E), central stations (40A–40B), and receiver modules (60A–60C). As would be obvious to one skilled in the art, other monitors for gathering biomedical information, such as ECG devices, may be used in place of or with transmitters (10A–10E). Each transmitter (10A–10E) is connected to a patient to obtain and measure biomedical information from the patient. The obtained information is later transmitted to one or more central stations (40A–40B) for processing, storage, and display. In a preferred embodiment, the display on one central station may be replicated on other central stations for redundancy.

According to the inventive system, transmitters (10A–10E) may be single use disposable transmitters and/or reusable transmitters and may operate in a hard wired or wireless environment. In a preferred embodiment of the system, transmitters (10A–10E) are wireless, disposable transmitters. Each disposable transmitter may be included in a kit with the appropriate wiring, batteries, electrodes, patient preparation supplies, such as alcohol and wipes, and instructions for setting up and using the disposable transmitters for easier management and maintenance.

In prior systems, reusable transmitters are configured by trained technical professionals. According to the inventive system, disposable transmitters may be configured in an automated and intuitive manner by clinical professionals who have little technical training. Thus, in the present invention, prior to using each disposable transmitter (10A–10E), the transmitter must be configured to work with one or more central stations (40A–40B) and one receiver module (60A–60C). In a preferred embodiment of the invention, central stations (40A–40B) may include one or more programming stations for configuring disposable transmitters (10A–10E). Alternatively, the programming stations may be separate from central stations (40A–40B). The programming stations allow the users of disposable transmitters (10A–10E) to configure them relatively quickly and easily without needing advanced technical information, such as available radio channels. In a preferred embodiment, each transmitter (10A–10E) is configured in its package at a central station (40A–40B) and taken to the patient's location for use on the patient. This procedure ensures easier management and maintenance of disposable transmitters (10A–10E).

After configuration, each transmitter (10A–10E) is connected to a patient to gather biomedical information from the patient. Information obtained by each transmitter (10A–10E) is delivered over a radio channel to one of several receiver modules (60A–60C). In a preferred embodiment of the invention, radio channels (80A–80E) are wireless channels. The information is then relayed over a wired system backbone (95) from the receiver modules (60A–60C) to the appropriate central station (40A–40B). In one embodiment, each receiver module (60A–60C) may be located in the same computer as a central station (40A–40B).

In order for the system to function properly, prior system configuration must be performed such that each disposable transmitter (10A–10E) is correctly programmed to transmit information via a dedicated wireless channel (80A–80E). According to the invention, each wireless channel (80A–80E) is configured to and used by one transmitter (10A–10E). The receiver module (60A–60C) that receives information from a transmitter also must be configured to the same wireless channel (80A–80E) as the transmitter, and the receiver module must be mapped to the appropriate central station (40A–40B), such that each patient's data is sent not only to the correct central station, but also to the correct area on the central station's monitor.

Figure 2:
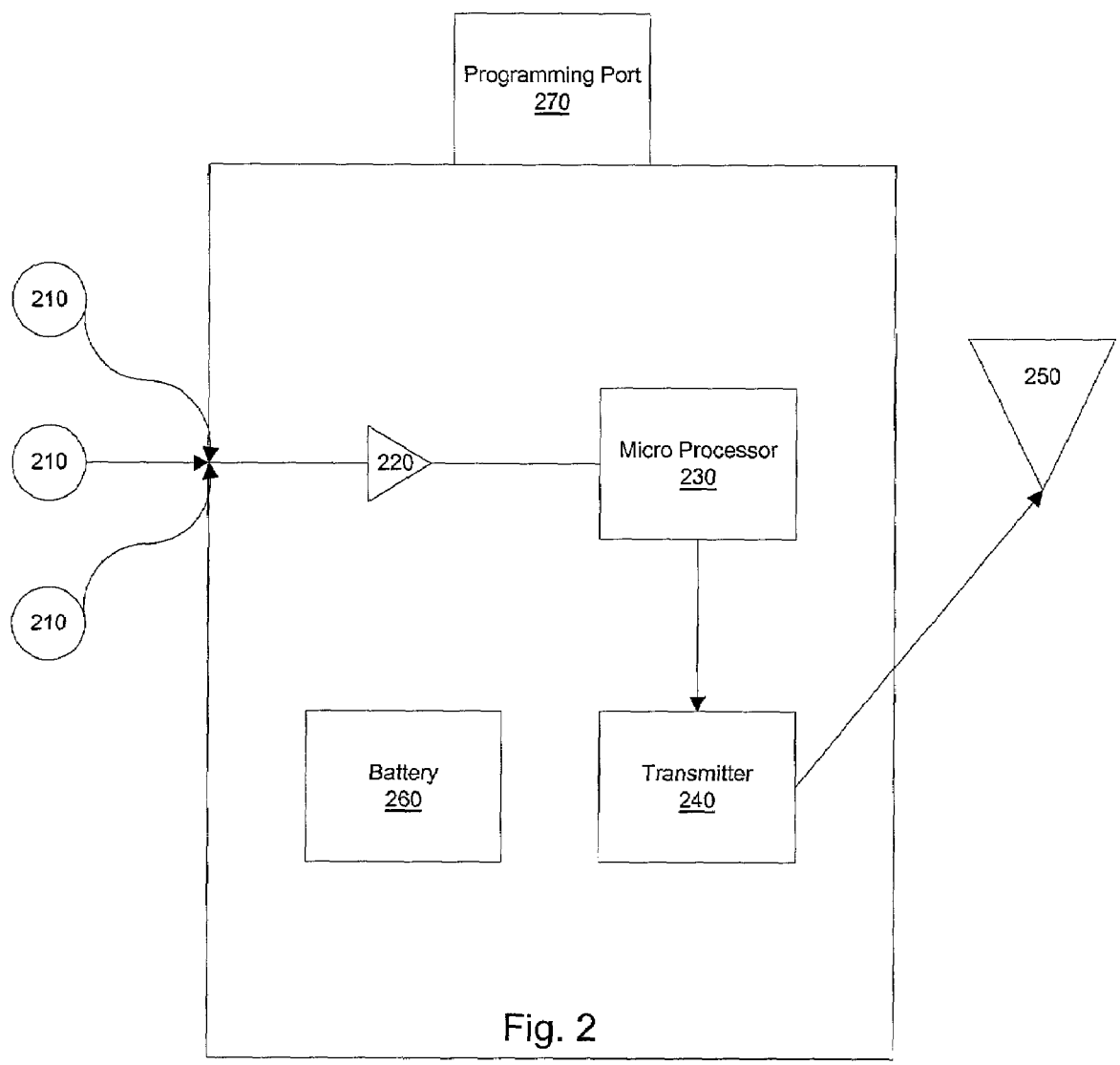
FIG. 2 illustrates a preferred embodiment of a disposable transmitter that is used in FIG. 1.

FIG. 2 illustrates a preferred embodiment of disposable transmitter (10A–10E) that is used in FIG. 1. In each disposable transmitter (10A–10E), biomedical data is gathered from the patient through a connection 210 that is in contact with the patient and the data is processed by a processing circuitry 220. The data is digitized and further processed by a microprocessor 230. Thereafter, the data is transmitted to a receiver module (60A–60C) via a frequency synthesized transmitter 240 and an antenna 250. In one embodiment, disposable transmitter (10A–10C) operates on a power supply, such as battery 260, and may be programmed or configured via a programming port 270. As may be obvious to one skilled in the art, other powering devices, such as electricity may be used in place of a battery.

In a preferred embodiment, the present invention includes an ECG monitor, such as that described in U.S. patent application Ser. No. 09/776,324, which is hereby incorporated by reference in its entirety.

According to the present invention, each transmitter (10A–10E) is marked with disposal instructions describing how to deactivate, recycle and/or dispose of the transmitter after use. Alternatively, each transmitter (10A–10E) may deactivate and disable itself after being disconnected from the patient for a predetermined period of time. After deactivation, electronics in the disposable transmitters (10A–10E) may be recycled. In a preferred embodiment, a stamped envelop that is pre-addressed with the address of a recycling facility is included with each new set of transmitters (10A–10E) for returning the transmitters for recycling after use. Upon receiving used transmitter (10A–10E), the sender is automatically credited and the circuit board is removed from used transmitter (10A–10E), cleaned and inserted into a new disposable transmitter. Recycled transmitters (10A–10E) are then shipped again and include a pre-addressed stamped envelope for recycling.

Figure 3:
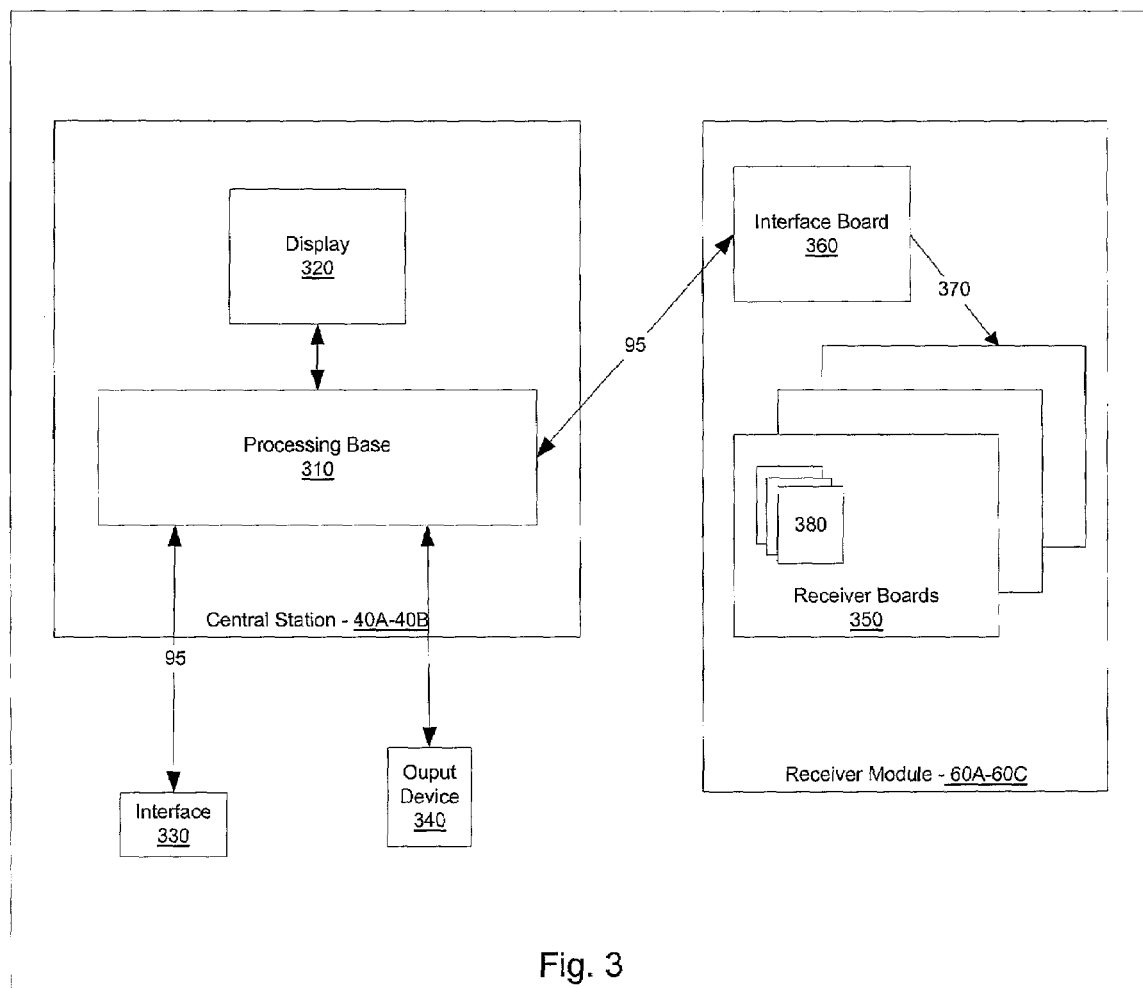
FIG. 3 illustrates a preferred embodiment of a central station and a receiver module used in FIG. 1.

FIG. 3 illustrates a preferred embodiment of central station (40A–40B) and receiver module (60A–60C). In a preferred embodiment, each central station (40A–40B) includes a processing base 310 and a display 320 having a touch screen. Processing base 310 processes and stores incoming data and operates display 320. In one embodiment, display 320 is in close proximity to transmitter (10A–10E) during system configuration. Processing base 310 also communicates with a transmitter programming interface 330 for programming and configuring transmitters (10A–10E), and an output device 340, such as a strip chart recorder, for generating print outs of biomedical data. According to the present invention, an operator may use a remote transmitter programming interface 330 to remotely program transmitter (10A–10E) and assign an associated patient to a location on the display. Processing base 310 also connects central station (40A–40B) to receiver modules (60A–60C) via wired system backbone 95.

Each receiver module (60A–60C) includes several wireless receiver boards 350 which are connected to an interface board 360 via an internal back-plane 370 which connects interface board 360 and receiver boards 350. After receiving data from transmitters, interface board 360 formats the data for further transmission to a central station (40A–40B). Each receiver board 350 includes one or more frequency synthesized receivers 380 which may be used to tune in data from a specific transmitter (10A–10E). When a transmitter is configured, an associated receiver board 350 also must be configured to tune the receiver module (60A–60C) to the correct frequency on the wireless channel that is associated with the transmitter. Thereafter, interface board 360 and processing base 310 must be configured to transmit data to the correct location on the display 320 and to the patient associated with that location.

Figure 4:
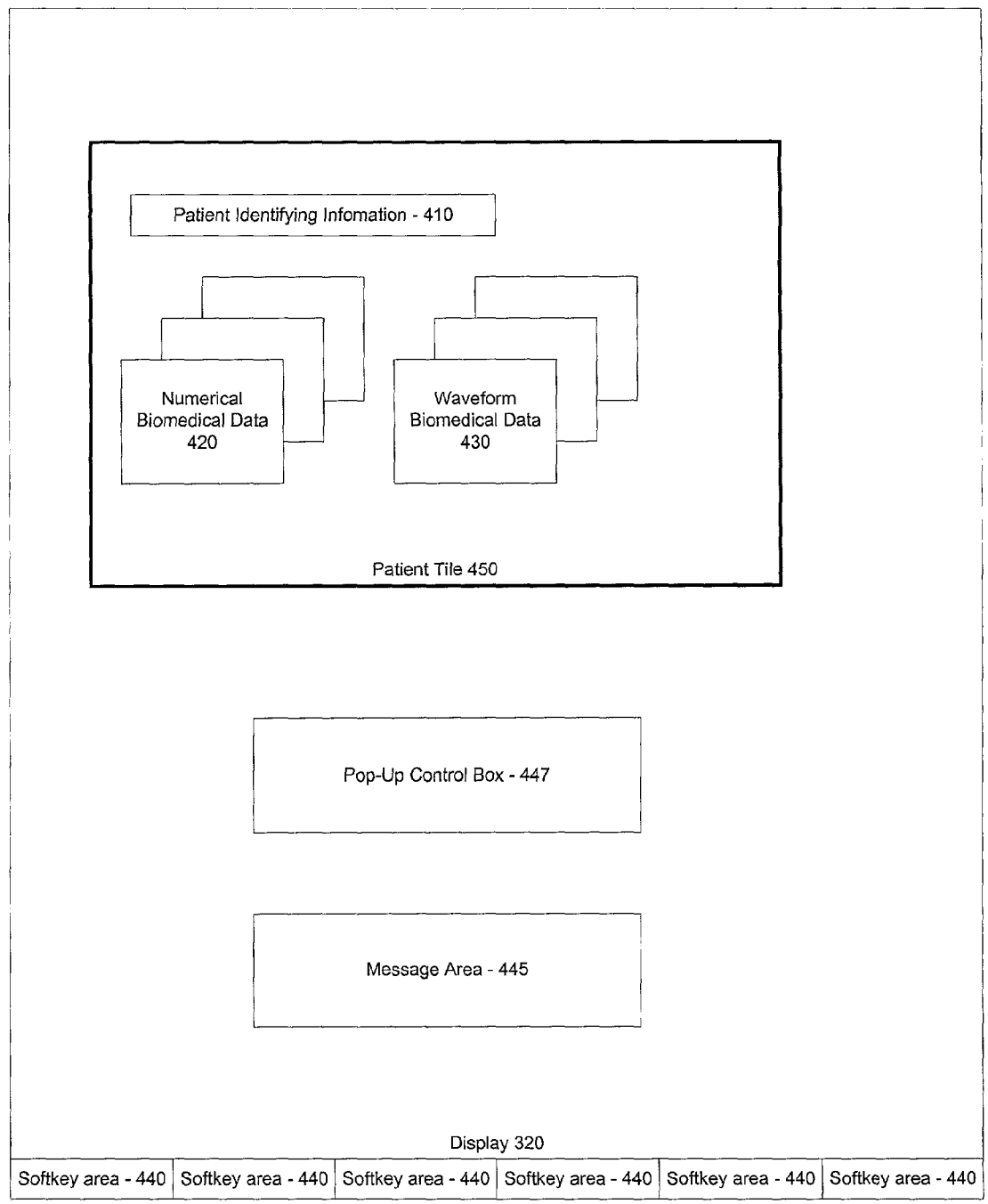
FIG. 4 illustrates a preferred embodiment of the central station's display format.

FIG. 4 illustrates a preferred embodiment of the central station display 320 format. Display screen 320 in central station (40A–40B) is divided into multiple patient tiles 450. Each patient tile 450 displays data transmitted from one patient and each tile may comprise several regions 410–430 that display patient information, such as identifying information, numerical biomedical data, and waveform biomedical data. According to the invention, each tile 450 is associated with a disposable transmitter (10A–10E) and also is associated with a specific radio frequency. The radio frequency represents a channel into which the receiver associated with the tile is tuned. Each time the system is started, each patient's tile 450 appears in the location it was during its previous operating period. During normal operations, the location and size of tile 450 is largely static and pre-determined. This enables the operator of the system to map a location on the display with a specific transmitter and ultimately a specific patient. In situations where a transmitter is associated with a specific location, the location may also be mapped to a specific tile through the associated transmitter. In other embodiments of the invention, it is possible for an operator of the display to resize and/or move tile 450 on display screen 320. As is obvious to one skilled in the art, the location and size of tile 450 are determined by the user of the system.

Display screen 320 also includes controls and instructions regions, such as a soft-key area 440 and a message area 445. Soft-key area 440 displays control keys that are used by the operator to control various features of central station (40A–40B). Message area 447 instructs and alerts users of the telemetry system to various system conditions. Display screen 320 may additionally employ one or more pop-up control boxes 447 to inform the operator of various conditions and instructions and to gather information from the operator.

Figure 5:
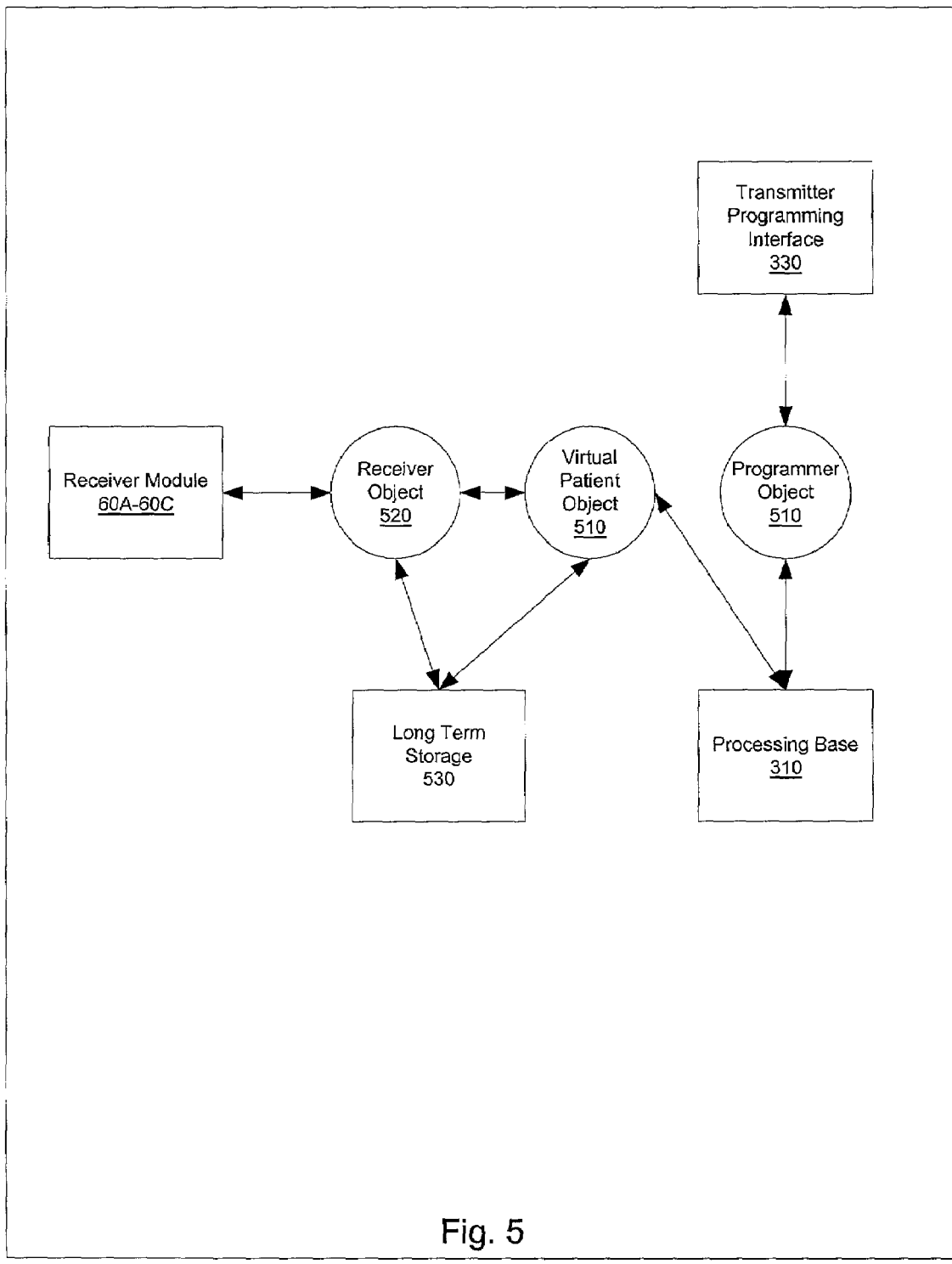
FIG. 5 illustrates a preferred embodiment of the software that is used to operate the central station.

FIG. 5 illustrates a preferred embodiment of the software that is used to operate central station (40A–40B). The software includes multiple Virtual Patient Objects (VPO) 510, whereby each patient's tile 450 is mapped to one VPO 510. Each VPO 510 also is mapped to one receiver object 520. In one embodiment of the invention, each VPO may be mapped directly and permanently to one tile 450 and to one receiver object 520. Each receiver object 520 maintains control of one receiver module (60A–60C) and receiver object 520 retains all information necessary to configure receiver module (60A–60C) to a fixed wireless channel (80A–80E). During normal operations, biomedical information from disposable transmitter (10A–10E) flows through receiver module (60A–60C) and receiver object 520 into memory in central station (40A–40B). Thereafter, the information is transmitted to VPO 510 for display in an associated patient tile 450.

According to the invention, each patient connected to a transmitter (10A–10E) is typically admitted to an active patient tile 450 in order to correctly associate the patient's identifying information with the biomedical information on the tile. A patient is admitted to tile 450 when the operator enters identifying patient information in tile 450. In some cases, however, a patient connected to a transmitter (10A–10E) may not be admitted to a patient tile 450. Nevertheless, VPO 510 associated with each tile 450 maintains knowledge of whether or not a patient is admitted to the tile. If a patient is admitted to the tile, VPO 510 retains the patient's identifying information.

Figure 6:
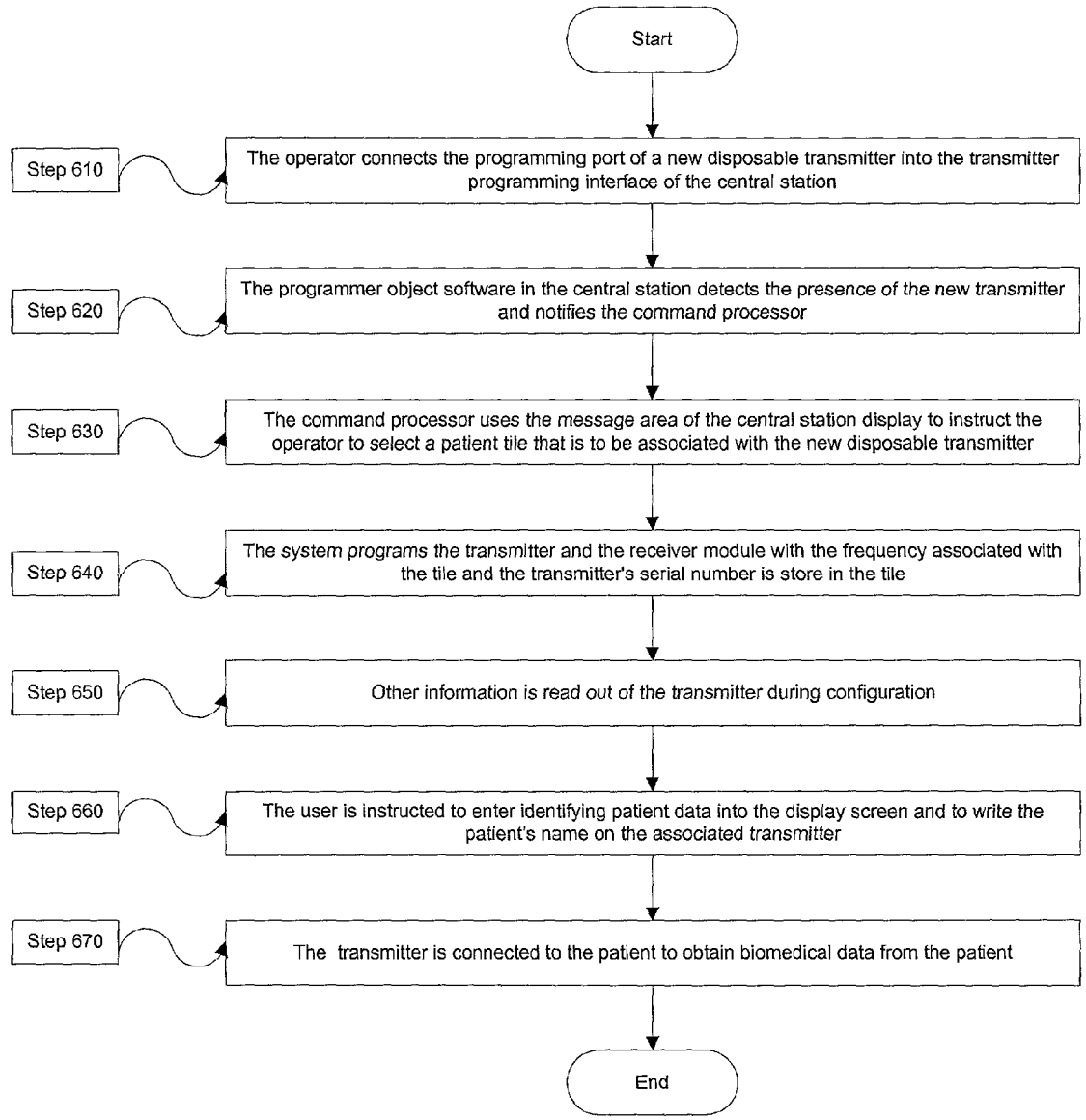
FIG. 6 illustrates a flow diagram which describes how to connect the first patient to the inventive system.

FIG. 6 illustrates a flow diagram that describes how to connect the first patient to the system according to the present invention. In Step 610, the operator connects programming port 270 of a new disposable transmitter 10A into transmitter programming interface 330 of a central station (40A–40B). At Step 620, the programmer object software in central station (40A–40B) detects the presence of new transmitter 10A and notifies command processor base 310. At Step 630, command processor base 310 uses the message area of central station's display 320 to instruct the operator to select patient tile 410A that is to be associated with new disposable transmitter 10A. In a preferred embodiment of the present invention, the operator selects patient tile 410A by touching a tile on display screen 320. Other methods, such as a mouse and/or a keyboard, may be used by the operator to select patient tile 410A. At Step 640, the system programs transmitter 10A and receiver module 60A with the frequency associated with tile 410A and the transmitter's serial number is stored in tile 410A. The transmitter's serial number is also included in transmitted data packets from transmitter 10A. Associated tile 410A uses the serial number to identify and only display data from transmitter 10A. At Step 650, other information, such as the software version of transmitter 10A, is also read out of transmitter 10A during configuration. At Step 660, the user is instructed to enter identifying patient data into display screen 320 and to write the patient's name on transmitter 10A. At Step 670, transmitter 10A is connected to the patient to obtain biomedical data from the patient.

Figure 7:
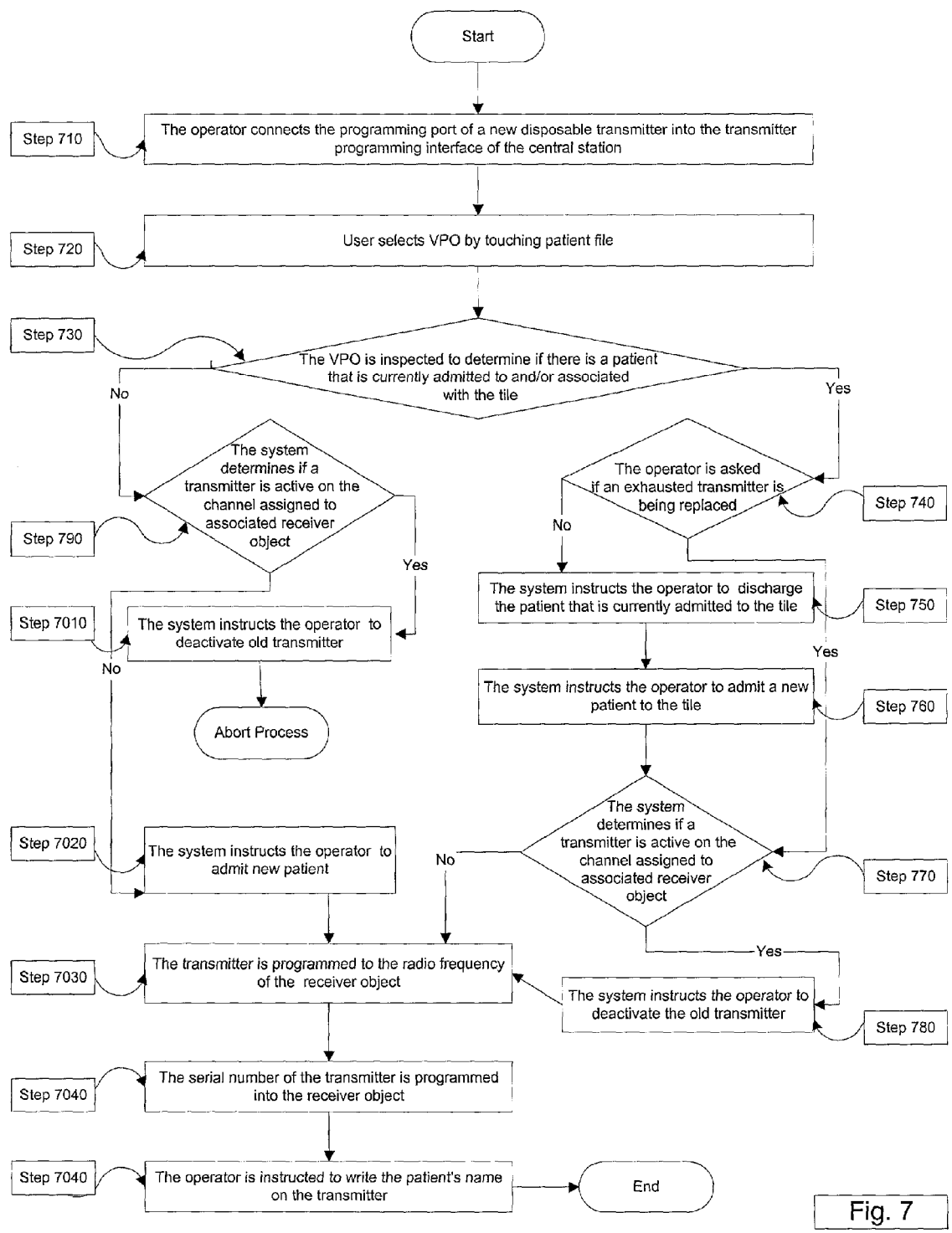
FIG. 7 illustrates a flow diagram which describes how to connect additional transmitters to the inventive system.

FIG. 7 illustrates a flow diagram that describes how to connect or disconnect one or more transmitters to the inventive system. At Step 710, the operator connects programming port 270 of new disposable transmitter 10B into transmitter programming interface 330 of central station 40. The programmer object software in central station (40A–40B) detects the presence of new transmitter 10B and notifies command processor base 310. Command processor base 310 reads transmitter 10B serial number and uses the message area of central station display 320 to instruct the operator to select patient tile 410B that is to be associated with new disposable transmitter 10B. In Step 720, the operator selects VPO 510, to be associated with transmitter 10B and patient tile 410B, by touching patient tile 410B.

In Step 730, once a selection has been made, VPO 510 is inspected to determine if there is a patient that is currently admitted to and/or associated with tile 410B. In Step 740, if there is already a patient admitted to tile 410B, the operator is asked if an exhausted transmitter is being replaced. In Step 750, if an exhausted transmitter is not being replaced, the system instructs the operator to first discharge the patient that is currently admitted to tile 410B. In Step 760, the operator is instructed to admit a new patient to tile 410B. In Step 770, if an exhausted transmitter is being replaced, the system determines if a transmitter is active on the channel assigned to associated receiver object 520. In Step 780, if there is an active transmitter on the channel, the system assumes that the operator is replacing the transmitter associated with tile 410B for a valid reason. The system then instructs the operator to remove the old transmitter before activating new transmitter 10B.

In Step 790, if there is no patient admitted to and/or associated with tile 410B, the system determines if a transmitter is active on the channel assigned to associated receiver object 520. In Step 7010, if there is an active transmitter on the channel, the system instructs the operator to remove the old transmitter before activating new transmitter 10B. In Step 7020, if there is no active transmitter on the channel, the system instructs the operator to admit the patient.

In Step 7030, transmitter 10B is programmed to the radio frequency of receiver object 520. In Step 7040, the serial number of transmitter 10B is read from its microprocessor 230 and programmed into the receiver object 520. At Step 7050, the operator is instructed to identify the patient on transmitter 10B, for example, to manually label (using for example, permanent marker and surgical tape) or electronically write (using the programming station) a patient's name and/or identification number on transmitter 10B.

FIG. 8 illustrates an embodiment of a telemetry system with one or more remote programming stations (810A–810C). Remote programming stations 810 may be included in several locations in the coverage area. For example, a coverage area may be a hospital with many floors. Central station (40A–40B) may be located on one floor and remote programming stations (810A–810C) may be located on other floors. In another example, the coverage area also may include locations that are different from the location where central station (40A–40B) is located. Therefore, remote programming stations (810A–810C) may be located in locations that are different from the location where central station (40A–40B) is located. Remote programming station (810A–810C) may be a mirror of central station's display 320, showing the same data and allowing the same interactions. Alternatively, the display associated with remote programming station (810A–810C) may show only data entered on that station. As would be obvious, remote stations could be programmed in various ways to display various information as required to meet a particular use of the system.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A configuration system for use with a plurality of patient monitors communicating with a central station, each patient monitor transmitting data from a given patient to the central station to be displayed on a display, the configuration system comprising a program that when executed by a computer causes the computer to:
   detect a presence of a patient monitor that is unconfigured;
   display a prompt to a user indicating the presence of the unconfigured patient monitor;
   accept from the user, a command linking data of the patient monitor to a portion of the display; and
   configure the patient monitor and central station to automatically display the data in the portion of the display.

2. The configuration system of claim 1 wherein the computer is further caused to prompt the user to mark the patient monitor with a patient identifier prior to associating the patient monitor with a patient.

3. The configuration system of claim 2 wherein the patient monitor includes a manually applied label identifying a patient, and the computer is further caused to prompt the user to indicate the patient with which the patient monitor will be associated prior to associating the patient monitor with a patient.

4. The configuration system of claim 1 wherein the computer is further caused to automatically program the patient monitor to transmit the data on a channel corresponding to the portion of the display indicated by the user command.

5. The configuration system of claim 1 wherein the computer is further caused to automatically store and display a serial number of the patient monitor in the portion of the display indicated by the user command.

6. The configuration system of claim 1 wherein the computer is further caused to automatically program the patient monitor to transmit packets of monitoring information along with an identifier corresponding to the portion of the display indicated by the user command.

7. The configuration system of claim 1 wherein the computer is further caused to display a prompt on the display to enter patient identifier data at least indicating a patient from which the data will be gathered.

8. The configuration system of claim 1 wherein the display includes a plurality of tiles apportioning the display and wherein the user command is at least partially communicated by touching a tile to command linking data of the patient monitor to the portion of the display corresponding to the tile.

9. The configuration system of claim 8 wherein each tile is configured to display monitoring information from one of a plurality of patient monitors.

10. The configuration system of claim 1 wherein the patient monitor is configured to be disposable.

11. The configuration system of claim 1 wherein the computer is further caused to detect radio transmissions from the unconfigured patient monitor to detect the presence of the patient monitor that is unconfigured.

12. A computer readable storage medium having stored thereon a computer program comprising instructions that, when executed by a computer, causes the computer to:
   detect a patient monitor that is not configured to communicate with a central station;
   display a prompt on a display requesting user-desired display parameters for displaying information received from the patient monitor at the central station;
   automatically configure the patient monitor according to user-desired display parameters; and
   prompt the user to mark the patient monitor with a patient identifier prior to associating the patient monitor with a patient.

13. The computer program of claim 12 wherein the user-desired display parameters include a portion of the display within which to display information received from the patient monitor at the central station.

14. The computer program of claim 13 wherein the computer is further caused to automatically program the patient monitor to transmit information at frequency corresponding to the portion of the display indicated by the user-desired display parameters.

15. The computer program of claim 13 wherein the computer is further caused to automatically store and display a serial number of the patient monitor in the portion of the display indicated by the user-desired display parameters.

16. The computer program of claim 13 wherein the computer is further caused to automatically program the patient monitor to transmit information to the central station in packets with an identifier corresponding to at least one of the portion of the display indicated by the user-desired display parameters and an identity of the patient monitor.

17. The computer program of claim 12 wherein the mark includes a manually applied label identifying a patient to which the patient monitor will be associated after being configured to communicate with the central station.

18. The computer program of claim 12 wherein the patient monitor is disposable.

* * * * *